(12) United States Patent
Hirano et al.

(10) Patent No.: US 6,555,713 B1
(45) Date of Patent: Apr. 29, 2003

(54) PROTECTION OF DI-T-BUTYL DICARBONATE AGAINST DECOMPOSITION

(75) Inventors: Naoki Hirano, Tokuyama (JP); Masako Saijo, Tokuyama (JP)

(73) Assignee: Tokuyama Corporation, Yamaguchi (JP)

(*) Notice: Subject to any disclaimer, the term of this patent is extended or adjusted under 35 U.S.C. 154(b) by 5 days.

(21) Appl. No.: 09/857,700

(22) PCT Filed: Oct. 3, 2000

(86) PCT No.: PCT/JP00/06881
§ 371 (c)(1),
(2), (4) Date: Jun. 8, 2001

(87) PCT Pub. No.: WO01/27066
PCT Pub. Date: Apr. 19, 2001

(30) Foreign Application Priority Data

Oct. 8, 1999 (JP) .......................................... 11-287818

(51) Int. Cl.$^7$ .............................................. C07C 68/08
(52) U.S. Cl. ........................ 568/261; 560/24; 560/157; 564/393
(58) Field of Search ............................ 558/261; 560/24, 560/157; 564/393

(56) References Cited

U.S. PATENT DOCUMENTS 4,565,648 A    1/1986   Kopp et al.

FOREIGN PATENT DOCUMENTS

| EP | A2256559 | 2/1988 |
|----|----------|--------|
| JP | A6419045 | 1/1989 |
| JP | A5310645 | 11/1993 |

*Primary Examiner*—Robert Gerstl
(74) *Attorney, Agent, or Firm*—Birch, Stewart, Kolasch & Birch, LLP

(57) ABSTRACT

The decomposition of di-t-butyl dicarbonate which is a thermally unstable compound is inhibited. To achieve the object, a hydrocarbon compound such as hexane, cyclohexane, 1-hexene or toluene and/or a chain ether compound such as diisopropyl ether or t-butyl methyl ether are/is used as a decomposition inhibitor for di-t-butyl dicarbonate.

3 Claims, No Drawings

PROTECTION OF DI-T-BUTYL DICARBONATE AGAINST DECOMPOSITION

This application is the national phase under 35 U.S.C. §371 of PCT International Application No. PCT/JP00/06881 which has an International filing date of Oct. 3, 2000, which designated the United States of America and was not published in English.

TECHNICAL FIELD

The present invention relates to the inhibition of, decomposition of di-t-butyl dicarbonate. More specifically, it relates to the inhibition of decomposition of di-t-butyl dicarbonate in liquid form.

BACKGROUND ART

Di-t-butyl dicarbonate is an important compound as a protective agent for an amino group in the synthesis of pharmaceuticals and agricultural chemicals.

However, di-t-butyl dicarbonate is a thermally unstable compound and gradually decomposes when stored in liquid form. Therefore, when it is to be stored, it has been necessary to store it in a low-temperature storage at temperatures lower than its melting point so as to keep it in solid form.

However, since the melting point of di-t-butyl dicarbonate is 22 to 23° C., solid di-t-butyl dicarbonate melts partially in use, thereby making it very difficult to handle. Therefore, to avoid the difficulty in handling the solid di-t-butyl dicarbonate, the compound must be used in liquid form by keeping it at temperatures higher than its melting point at all times. However, when the compound is kept in liquid form for a long time, the decomposition as described above cannot be avoided.

Further, since it is complicated from an industrial point of view as well to melt the compound in solid form, those who use the compound on a large scale has desired to obtain the compound in liquid form. However, heretofore, such desire has been difficult to fulfill for maintaining the quality of the compound.

Therefore, a method for inhibiting the decomposition of di-t-butyl dicarbonate in liquid form has been desired.

DISCLOSURE OF THE INVENTION

The present inventors have made intensive studies to solve the above problems. As a result, they have found that the decomposition of di-t-butyl dicarbonate can be inhibited by adding a hydrocarbon compound and/or a chain ether compound to di-t-butyl dicarbonate and have therefore completed the present invention.

That is, firstly, the present invention relates to a mixed composition consisting essentially of (a) di-t-butyl dicarbonate and (b) at least one compound selected from the group consisting of a hydrocarbon compound and a chain ether compound.

Further, secondly, the present invention relates to the use of at least one compound selected from a group consisting of a hydrocarbon compound and a chain ether compound for inhibiting the decomposition of di-t-butyl dicarbonate.

Still further, thirdly, the present invention relates to the use of the mixed composition of the present invention for protecting the amino group of an amino group-containing compound by a t-butoxycarbonyl group.

PREFERRED EMBODIMENTS OF THE INVENTION

Preferred embodiments of the present invention will be described in detail hereinafter.

In the present invention, a compound used for inhibiting the decomposition of di-t-butyl dicarbonate (to be sometimes referred to as "decomposition inhibitor" hereinafter) is a hydrocarbon compound or a chain ether compound.

As the hydrocarbon compound in the present invention, a known compound which comprises carbon and hydrogen and which can be kept in liquid or solid form at room temperature and atmospheric pressure can be used without any limitation.

The hydrocarbon compound is preferably a saturated aliphatic hydrocarbon having 5 to 16 carbon atoms, an unsaturated aliphatic hydrocarbon having 5 to 16 carbon atoms or an aromatic hydrocarbon having 6 to 18 carbon atoms. Of these, a saturated aliphatic hydrocarbon having 5 to 9 carbon atoms, an unsaturated aliphatic hydrocarbon having 5 to 9 carbon atoms and an aromatic hydrocarbon having 6 to 7 carbon atoms are more preferable.

Illustrative examples of the hydrocarbon compound include saturated aliphatic hydrocarbons having 5 to 16 carbon atoms such as pentane, 2-methylbutane, hexane, 2-methylpentane, 2,2-dimethylbutane, 2,3-dimethylbutane, heptane, 2,2,3-trimethylpentane, octane, isooctane, nonane, 2,2,5-trimethylhexane, decane, undecane, dodecane, tridecane, tetradecane, hexadecane, cyclopentane, methylcyclopentane, cyclohexane, methylcyclohexane, ethylcyclohexane, p-menthane and bicyclohexyl; unsaturated hydrocarbons having 5 to 16 carbon atoms such as 1-hexene, 1-pentene, 1-octene, 1-heptene, 1-nonene, 1-decene, 1-undecene, 1-dodecene, 1-tridecene, 1-tetradecene, 1-hexadecene, cyclohexene, α-pinene and dipentene; and aromatic hydrocarbons having 6 to 18 carbon atoms such as benzene, toluene, o-xylene, m-xylene, p-xylene, ethylbenzene, cumene, mesitylene, naphthalene, tetralin, butyl benzene, p-cymene, cyclohexyl benzene, diethyl benzene, pentyl benzene, dipentyl benzene, dodecyl benzene, biphenyl and styrene.

Of these, saturated aliphatic hydrocarbons having 5 to 9 carbon atoms such as pentane, 2-methylbutane, hexane, 2-methylpentane, 2,2-dimethylbutane, 2,3-dimethylbutane, heptane, 2,2,3-trimethylpentane, octane, isooctane, 2,2,5-trimethylhexane, cyclopentane, methylcyclopentane, cyclohexane, methylcyclohexane and ethylcyclohexane; unsaturated aliphatic hydrocarbons having 5 to 9 carbon atoms such as 1-hexene, 1-pentene, 1-octene, 1-heptene and 1-nonene; and aromatic hydrocarbons having 6 or 7 carbon atoms such as benzene and toluene are suitably used in that their effect of inhibiting the decomposition is high.

As the chain ether compound in the present invention, a known compound in which two hydrocarbon groups are bonded to an oxygen atom and which can be kept in liquid or solid form at room temperature and atmospheric pressure can be used without any limitation. An example of the compound is an ether compound represented by the following formula (1):

$$R^1\text{—O—}R^2 \tag{1}$$

wherein $R^1$ and $R^2$ independently represent an alkyl group having 2 to 6 carbon atoms or an alkenyl group having 2 to 6 carbon atoms.

Of these, a dialkyl ether having 4 to 8 carbon atoms is preferable.

Illustrative examples of the chain ether compound include chain ether compounds having 4 to 12 carbon atoms such as diethyl ether, dipropyl ether, diisopropyl ether, dibutyl ether, t-butyl methyl ether, di-t-butyl ether, dihexyl ether, ethyl vinyl ether and butyl vinyl ether.

Of these, dialkyl ether compounds having 4 to 8 carbon atoms such as diethyl ether, dipropyl ether, diisopropyl ether, dibutyl ether, t-butyl methyl ether and di-t-butyl ether are suitably used in that their effect of inhibiting the decomposition is high.

All of these hydrocarbon compounds and chain ether compounds can be obtained easily as reagents and industrial raw materials.

These decomposition inhibitors may be used solely or in combination of two or more as required.

Although the decomposition inhibitor is not limited to a particular amount, it should be used in such an amount that ensures that the concentration of the decomposition inhibitor should be 0.1 to 95 wt %, preferably 1 to 80 wt %, based on the total amount of di-t-butyl dicarbonate and the decomposition inhibitor to obtain a satisfactory effect of inhibiting the decomposition. Therefore, the concentration of di-t-butyl dicarbonate is 99.9 to 5 wt %, preferably 99 to 20 wt %, based on the total amount of di-t-butyl dicarbonate and the decomposition inhibitor.

As a method of mixing the decomposition inhibitor and di-t-butyl dicarbonate, a conventional mixing method can be used without any limitation. However, it is preferable that they be mixed by stirring or the like to form a homogeneous mixture. In this case, they can be charged into a mixing container simultaneously or successively and then mixed.

As for the mixing temperature, when it is too high, di-t-butyl dicarbonate decomposes. It is generally 50° C. or lower, preferably 30° C. or lower.

To store the mixture, it is put in a closed container, an inert gas is introduced into the container, and the container is stored in a cool, dark place.

As for the storage temperature, when it is too high, a satisfactory effect of inhibiting the decomposition cannot be obtained, and di-t-butyl dicarbonate decomposes. It is generally 30° C. or lower, preferably 10° C. or lower.

A decomposition inhibitor obtained as a reagent or an industrial raw material may be used directly as the decomposition inhibitor used in the present invention. In some cases, however, it may be dehydrated and purified by such procedures as distillation.

The amount of water contained in the decomposition inhibitor is generally 30,000 ppm or less, preferably 10,000 ppm or less, to obtain a satisfactory effect of inhibiting the decomposition.

Further, the decomposition inhibitor should not contain such impurities as peroxides, acids and bases. When the decomposition inhibitor is used with these impurities contained therein, it should be purified to such an extent that ensures that the peroxides cannot be detected by a color identification test using potassium iodide and that the amounts of the acids and bases should be 1,000 ppm or less, preferably 100 ppm or less.

Although the purity of di-t-butyl dicarbonate used in the present invention is not particularly limited, it should be generally 90% or higher, preferably 95% or higher to obtain a satisfactory effect of inhibiting the decomposition.

The amount of water contained in di-t-butyl dicarbonate is generally 30,000 ppm or less, preferably 10,000 ppm or less, to obtain a satisfactory effect of inhibiting the decomposition.

Therefore, the water content of the mixed composition of the present invention is preferably 30,000 ppm at most, more preferably 10,000 ppm at most.

Further, the contents of acids, bases or both in the mixed composition of the present invention are preferably 1,000 ppm at most, more preferably 100 ppm at most.

The use of the hydrocarbon compound and the chain ether compound as a decomposition inhibitor for di-t-butyl dicarbonate is provided for the first time by the present invention.

The mixture in the present invention which comprises the hydrocarbon compound and/or the chain ether compound and. di-t-butyl dicarbonate has the advantage that it can be directly used in the reaction of protecting an amino group in organic synthesis without removing the decomposition inhibitor contained in the mixture. That is, the mixed composition of the present invention can be used for protecting the amino group of an amino group-containing compound by a t-butoxycarbonyl group, and, in that case, the mixed composition can be directly used in the protection reaction. As a matter of course, when the presence of the decomposition inhibitors is undesirable, the mixed composition may be used after the hydrocarbon compound and/or the chain ether compound are/is removed by such procedures as distillation.

EXAMPLE

The present invention will be further described with reference to Examples hereinafter. However, it should not be limited thereby in any way.

Example 1

50 g of di-t-butyl dicarbonate (purity: 99.3%, water content: 85 ppm) was charged into a 200-ml flask, and 50 g of hexane (purity: 98.1%, water content: 111 ppm) was then charged therein. The mixture was kept at 50° C. under agitation. After 200 hours, naphthalene was added as an internal standard substance, and the residual amount of di-t-butyl dicarbonate was quantified by gas chromatography (column: HP-5, product of Hewlett-Packard Company, detector: FID, carrier gas: helium) to determine its decomposition rate, which was found to be 0.5%.

Examples 2 to 14

The decomposition rates of di-t-butyl dicarbonate were measured in the same manner as in Example 1 using the compounds listed in Table 1. The results are shown in Table 1.

TABLE 1

| Example | Added compounds | Purity of added compounds (%) | Water content of added compounds (ppm) | Amounts of added compounds (wt %)* | Decomposition rate of di-t-butyl dicarbonate (%) |
|---|---|---|---|---|---|
| 2 | heptane | 98.2 | 89 | 50 | 0.5 |
| 3 | toluene | 99.9 | 104 | 50 | 2.3 |
| 4 | cyclohexane | 99.9 | 110 | 50 | 1.7 |
| 5 | 1-hexene | 98.1 | 105 | 50 | 1.5 |
| 6 | t-butyl-methyl ether | 99.9 | 356 | 50 | 1.0 |
| 7 | diisopropyl ether | 99.7 | 516 | 50 | 0.7 |
| 8 | hexane | 98.1 | 111 | 80 | 0.4 |
| 9 | hexane | 98.1 | 111 | 20 | 0.5 |
| 10 | hexane | 98.1 | 111 | 10 | 0.6 |
| 11 | hexane | 98.1 | 111 | 5 | 1.4 |
| 12 | hexane | 98.1 | 111 | 3 | 2.0 |

TABLE 1-continued

| Example | Added compounds | Purity of added compounds (%) | Water content of added compounds (ppm) | Amounts of added compounds (wt %)* | Decomposition rate of di-t-butyl dicarbonate (%) |
|---|---|---|---|---|---|
| 13 | diisopropyl ether | 99.7 | 516 | 30 | 0.7 |
| 14 | diisopropyl ether | 99.7 | 516 | 10 | 2.0 |

*The total amount of di-t-butyl dicarbonate and the added compound is 100 wt%.

Comparative Examples 1 to 7

The decomposition rates of di-t-butyl dicarbonate were measured in the same manner as in Example 1 using the compounds listed in Table 2. The results are shown in Table 2.

TABLE 2

| Comparative Example | Added compounds | Purity of added compounds (%) | Water content of added compounds (ppm) | Amounts of added compounds (wt %)* | Decomposition rate of di-t-butyl dicarbonate (%) |
|---|---|---|---|---|---|
| 1 | none | 0 | 0 | 0 | 4.5 |
| 2 | isobutyl methyl ketone | 99.9 | 249 | 50 | 4.6 |
| 3 | ethyl acetate | 99.9 | 81 | 50 | 4.6 |
| 4 | chloroform | 99.9 | 91 | 50 | 7.1 |
| 5 | tetrahydrofuran | 99.9 | 754 | 50 | 6.0 |
| 6 | 1,2-dimethoxyethane | 99.9 | 280 | 50 | 9.7 |
| 7 | 1,4-dioxane | 99.9 | 165 | 50 | 5.3 |

*The total amount of di-t-butyl dicarbonate and the added compound is 100 wt %.

What is claimed is:

1. A method for suppressing the decomposition of di-t-butyl dicarbonate in storage, which comprises storing di-t-butyl dicarbonate as a solution in at least one compound selected from the group consisting of a saturated aliphatic hydrocarbon having 5 to 9 carbon atoms, unsaturated aliphatic hydrocarbon having 5 to 9 carbon atoms, aromatic hydrocarbon having 6 to 7 carbon atoms and dialkyl ether having 4 to 8 carbon atoms, said solution having a water content of 30,000 ppm at most.

2. The method of claim 1, wherein said solution is kept in a sealed vessel.

3. A method for protecting an amino group of an amino group-containing compound which comprises mixing a composition consisting essentially of (a) di-t-butyl dicarbonate and (b) at least one compound selected from the group consisting of a saturated aliphatic hydrocarbon having 5 to 9 carbon atoms, unsaturated aliphatic hydrocarbon having 5 to 9 carbon atoms, aromatic hydrocarbon having 6 to 7 carbon atoms and dialkyl ether having 4 to 8 carbon atoms, and having a water content of 30,000 ppm at most with said amino group-containing compound.

* * * * *